United States Patent [19]

Austad

[11] Patent Number: 4,872,450
[45] Date of Patent: Oct. 10, 1989

[54] WOUND DRESSING AND METHOD OF FORMING SAME

[76] Inventor: Eric D. Austad, 309 Riverview Dr., Ann Arbor Township, Washington County, Mich. 48105

[21] Appl. No.: 759,628

[22] Filed: Jul. 26, 1985

Related U.S. Application Data

[63] Continuation-in-part of Ser. No. 641,813, Aug. 17, 1984, abandoned.

[51] Int. Cl.⁴ .............................................. A61F 5/04
[52] U.S. Cl. ...................................... 128/90; 128/156
[58] Field of Search .................... 128/89, 90, 82, 155, 128/156, 157, DIG. 20

[56] References Cited

U.S. PATENT DOCUMENTS 3,563,234  2/1971  Fryer ...................................... 128/90
3,631,854  1/1972  Umstead ............................... 128/90

Primary Examiner—John D. Yasko
Attorney, Agent, or Firm—Harness, Dickey & Pierce

[57] ABSTRACT

A conforming foam wound dressing and the method of forming it, wherein an enclosure is placed over the wounded area, an opening is formed in the enclosure and medical grade foam is injected through the opening. The foam is dispensible from a pressurized container and dries rapidly to form a solid body.

2 Claims, 1 Drawing Sheet

U.S. Patent    Oct. 10, 1989    4,872,450
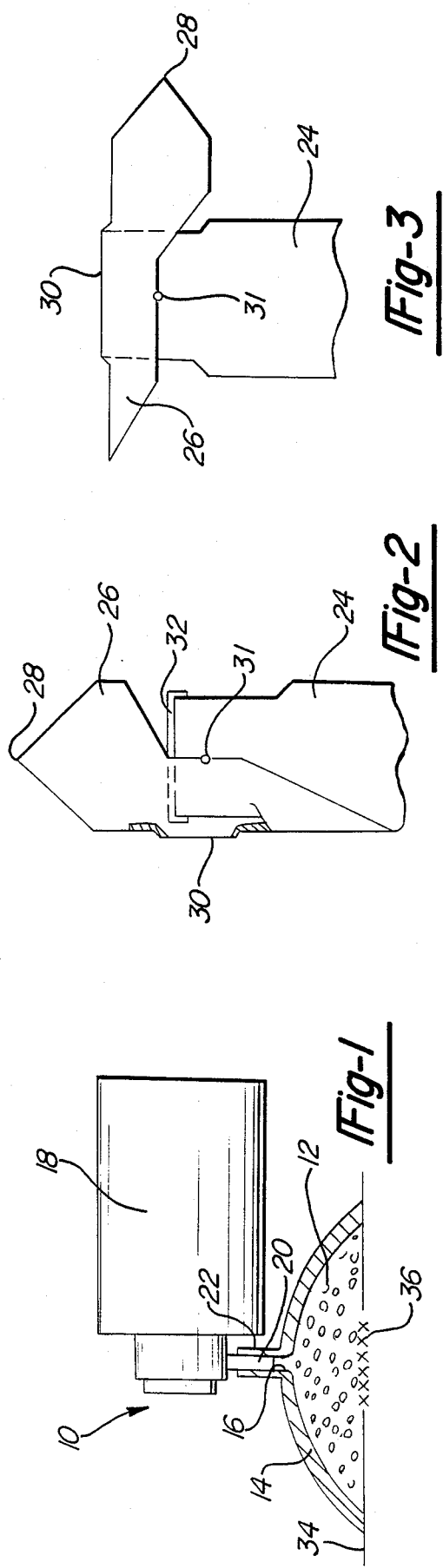
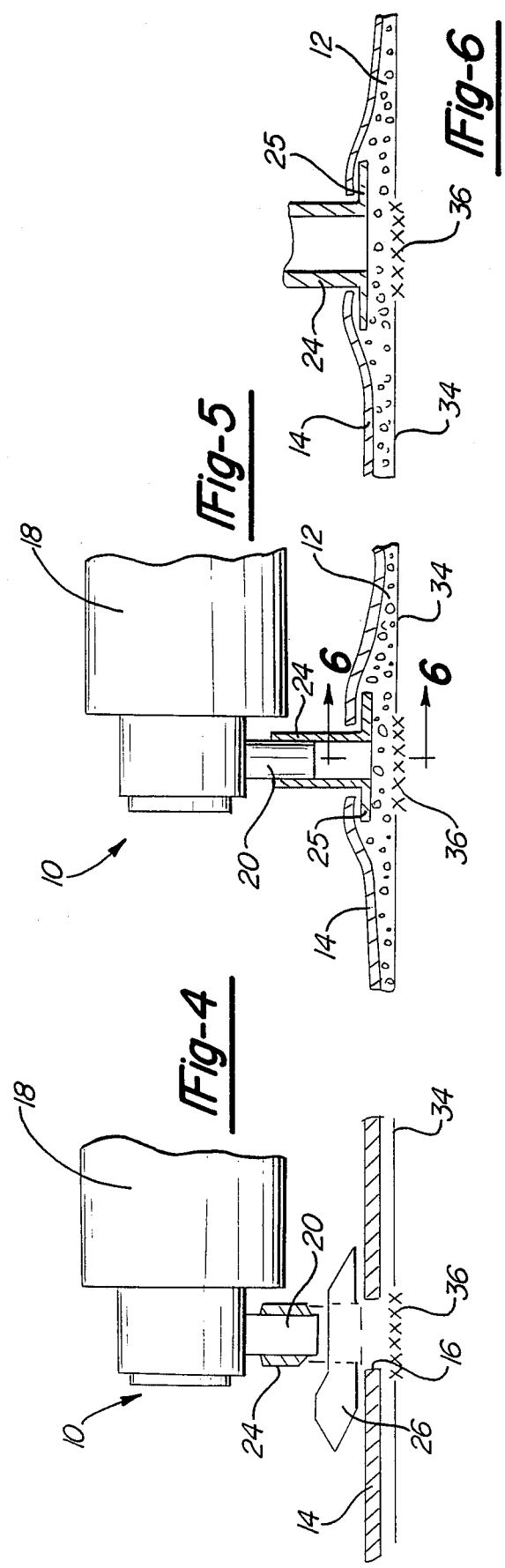

WOUND DRESSING AND METHOD OF FORMING SAME

CROSS REFERENCE TO RELATED APPLICATION

This application is a continuation-inpart of application Ser. No. 641,813 filed Aug. 17, 1984 now abandoned.

BACKGROUND OF THE INVENTION

This invention relates to the treatment of physical injuries such as cuts, burns, fractures, and surgical wounds. Perhaps the simplest and most widely used treatment is the common bandage. Bandages vary greatly in size, construction and use. They range in size from the small type covering shallow minor surface wounds and burns to the large surgical dressing type. These bandages are typically constructed of gauze material which may be layered several times. They may be attached to the skin with adhesive or wrapped around the injured area and attached with clips or the like. The advantages of common bandages are that they are inexpensively, widely available and applicable by unskilled persons. Thus, a bandage is frequently the first form of treatment received by an injured person.

However, bandages are disadvantageous in that they are permeable to gases and liquids and thus are inadequate to maintain a sterile environment around the wound. Also bandages are inadequate to remove blood and drainage from the area of the wound. Sticking of the wound to the bandage may cause pain and reinjury of the wound upon removal of the bandage. Finally, bandages may provide inadequate cushioning of the wound against bumps and scrapes, and are often time-consuming or complex to apply.

Numerous attempts have been made to overcome the disadvantages of the common bandage. For example, U.S. Pat. Nos. 3,419,506 and 3,572,330, describe a protective foam resin which is applied directly to a wound. The foam is sprayed onto the wound from a pressurized container and is thereafter spread and patted down manually by the person applying the foam. The foam dries rapidly to form a solid body which covers the wound. This type of treatment is advantageous in that the solidified foam provides a protective cushion for the wound. Also, blood and drainage can be dispersed into the foam and antibiotics may be introduced into the foam, thus enhancing the healing process. However, the foam can be difficult to apply since it may adhere to the applicant's hands and, since it is not confined, can spread or run off to areas where it is not needed. Furthermore, the resulting dressing may not be aesthetically pleasing.

Another type of treatment is described in U.S. Pat. Nos. 3,367,332 and 3,874,387. An expandible membrane or cap-shaped cover is placed over the wound and attached to the skin. Openings are provided in the membrane through which blood can be drained from the wound or fluids admitted to the wound area. Niether of these patents describes, however, an enclosure which is adaptable to receive medical grade foam from a pressurized container, and both are limited to other specific applications. This type of treatment does not, therefore, embody the advantages inherent in the foam-type dressing.

Patent 3,563,234 discloses a splint for a fractured limb and utilizes foam injected into a flexible perforated sleeve.

None of the aforementioned types of treatment is compatible with the use of common bandages and the like.

It is an object of the present invention, therefore, to provide a treatment in which medical grade foam is applied within a confining enclosure. It is another object of this invention to provide a wound dressing and a method of forming same which are compatible with common bandages which are generally flat and can be manipulated to confine the foam. SUMMARY OF THE INVENTION The present invention provides a conforming foam wound dressing which consists of a layer of medical grade foam covering the area of the wound, an enclosure which covers the foam layer and an opening in the enclosure through which the foam can be injected. Suitable foam resins are those which can be dispensed in substantially liquid form from a pressurized container and which dry rapidly to form a solid body. Examples include foams of the type described in U.S. Pat. Nos. 3,419,506 and 3,572,330, which patents are incorporated herein by reference. Foams of different chemical compositions, viscosities and durometer values may be used as desired for specific applications.

The enclosure may taken one of several forms. For example, the enclosure may consist simply of a common flat bandage or pad. In applying the dressing, the bandage is first cut or torn to form an opening therein. The foam is dispensed through the opening and solidifies in place between the bandage and the wound. In an alternative embodiment, the enclosure consists of a flexible diaphragm or dressing with an opening formed therein. A hollow stem is placed in the opening and communicates with the outlet of the pressurized container. In applying the dressing, the diaphragm is simply held in place over the wound or is secured to the adjoining skin, such as by adhesive. The foam is then introduced through the opening and solidifies in place between the diaphragm and the wound. Several materials are suitable for the construction of the diaphragm. In a preferred embodiment, the diaphragm is constructed of a felt-like material which may be cut to cover various sizes of wounds.

The invention is well adapted for use in the dressing of large wounds. A large diaphragm may be used, or smaller diaphragm assemblies may be placed at various sites over the wound. Where bandages are used to cover a large wound, the bandages may simply be cut foam inserted at several places.

Wound dressings of the type disclosed herein are especially useful in multi-casualty situations. In such situations, many of the persons to be treated have received initial treatment in the foam of bandages. Removal of the bandages in order to effect further treatment results in unnecessary pain and waste of precious time. The wound dressing of this invention is easily and quickly applied to existing bandages. Bandages are simply torn or cut and foam dispensed through an intermediate tube. Where bandages are not used in the initial treatment, or where foam is available for use in the initial treatment, bandages may be applied at that point or diaphragm assemblies may be used. A diaphragm of the appropriate size can easily and quickly be chosen or formed.

The treatment provides a sterile environment for the wound and seals the wound from the surrounding atmosphere. Blood and drainage are easily dispersed into the foam, and the foam provides a vehicle for antibiotics. Furthermore, since the foam is inserted into a confined area, substantial pressure can be built up within the dressing to thereby retard the flow of blood out of the wound. The enclosure also serves to confine the foam to a specified area, so that it is not necessary for the applicant to manually pat the foam down after dispensing it from the pressurized container. In addition, the solid body serves as a cushion for the wound, and may serve to immobilize the injured part of the body.

Further objects, features and advantages of this invention will become apparent from a consideration of the appended claims, the following description and the accompanying drawing in which:

FIG. 1 is a side sectional view of one embodiment of the wound dressing of this invention, wherein a diaphragm is employed to enclose the foam body;

FIG. 2 is an enlarged side view of an intermediate tube which is adapted to communicate with the nozzle of a pressurized foam dispenser;

FIG. 3 is an enlarged side view of the intermediate tube with the tip thereof rotated to allow passage of foam;

FIG. 4 is a side sectional view of a wounded area of skin with a bandage attached, prior to the injection of foam into the wound area;

FIG. 5 is a side sectional view similar to FIG. 4 but showing the wound area subsequent to the injection of foam; and FIG. 6 is a side sectional view of the wound area subsequent to the injection of foam, as seen from substantially the line 6—6 in FIG. 5.

DESCRIPTION OF THE PREFERRED EMBODIMENT

With reference to the drawings, the wound dressing of this invention, indicated generally at 10, consists of a foam body 12, an enclosure 14 which covers the foam body 12 and an opening 16 in the enclosure 14 through which the foam can be injected. The enclosure 14 may be produced from a variety of materials and is of a generally flat or cup shape that can be placed over a generally flat area of skin that contains a wound that must be bandaged. The enclosure 14 may consist of a flexible diaphragm, as seen in FIG. 1, or the enclosure 14 may also consist of a conventional pad or bandage, as seen in FIGS. 4-6.

The foam body 12 consists of a medical grade polymeric foam which is dispensed in substantially liquid form from a pressurized container 18. The foam is of the type that dried rapidly to form the solid body 12. The invention is not limited to a particular type of foam and in practice it will not be necessary to use different foams, that is, foams of varying chemical compositions, viscosities and durometer values, in different situations. The pressurized container 18 may consist of a conventional aerosol can which includes a valved nozzle 20 through which the foam is dispensed.

The foam may be conveyed from the container 18 to the wound area through a variety of means. For example, the nozzle 20 may be inserted directly into the enclosure opening 16. Where a diaphragm is used as in FIG. 1, a stem 22 may be provided at the opening 16. The container nozzle 20 is inserted into the stem 22 which directs the flow of foam into the enclosure. After the foam is injected, the stem 22 can be removed or left in place. Another alternative is to provide an intermediate tube 24 which can be attached to the container nozzle 20 and extend into the enclosure opening 16. The intermediate tube 24 may consist of a hollow cylinder or conventional surgical tubing or the like. As seen in FIGS. 5 and 6, it may be desirable to provide a flange 25 at the end of the tube 24 to block egress of foam during application.

In a preferred embodiment, as seen in FIGS. 2-4, the intermediate tube 24 has a rotational tip 26. The tip 26 has a sharpened end portion 28 which can be used to punctuate the enclosure 14 to thereby form the opening 16. An opening 30 is provided on the tip 26 through which the foam can pass. The tip 26 is rotated about a pin 31 approximately 90 degrees so as to provide an elongated flat surface which adds stability to the container 18 while the foam is being dispensed. A cap 32 may be placed over the end of the tube 24 to seal the contents from the environment.

In FIGS. 1, 4, 5 and 6, the wounded area of skin is indicated at 36 and the skin surface is indicated at 34. The method of forming the wound dressing 10 and applying it to the wound area 36 is as follows. First, an enclosure 14 is selected that is slightly larger than the wound. The enclosure 14 is then applied to the skin surface 34 so as to cover the wound area 36. The enclosure 14 may be attached to the skin surface 34, such as by adhesive or clipping, or it may be held in place manually while the foam is injected. Second, the opening 16 is formed in the enclosure 14. This may be done by cutting or tearing the enclosure 14. In an alternative embodiment, the opening 16 is formed in the enclosure 14 before it is applied to the skin surface 34. The opening 16 need not be formed in the enclosure 14 at a position directly above the wound 36. Third, the foam is injected through the opening 16 so that it is contained between the skin surface 34 and the enclosure 14. The enclosure is manipulated to facilitate this containment function. The foam dries rapidly to form the body 12. After the foam solidifies, the enclosure 14 may then be removed or retained in place.

The invention thus provides an improved wound dressing 10 and an improved method of forming the wound dressing 10. Medical grade foam is dispensed from a pressurized container 18 into a confining enclosure 14 and solidifies to form a body 12 which covers the wound. The foam body 12 protects the wound from the surrounding atmosphere, provides a cushion for the wound, and in general, enhances the healing process. The enclosure 14 aids application of the foam, holds the foam solidly in position, and provides an aesthetically-pleasing appearance.

What is claimed is:

1. A dressing for a skin wound of the type having blood and drainage associated therewith, said dressing being of a size slightly larger than said wound and having a surface substantially covering said wound and engaging a continuous area of the skin around the wound and generally in the plane of the skin around the wound, to thereby form an enclosure for the wound, said enclosure having an opening in said surface forming a conduit through which foam can be injected so as to directly engage the wound, and a layer of medical grade foam directed through said conduit into engagement with said skin and contained thereagainst by said surface of said dressing in a covering relation with said wound at a position disposed between said wound and said enclosure, whereby the foam not only provides a protective cushion for the wound but also a volume for absorbing blood and drainage from the wound, and a medium into which antibiotics can be introduced.

2. A method for dressing a skin wound of the type having blood and drainage associated therewith comprising the steps of:
   a. covering a continuous and generally flat circumferential area of the skin around the skin wound with an enclosure which engages the skin area and has a surface with an opening in said surface forming a conduit through which foam can be injected into direct engagement with the wound;
   b. injecting through said conduit a medical grade foam of the type dispensable in substantially liquid form from a pressurized container and which dries rapidly to form a solid body, into engagement with said skin area in a covering relation with said wound at a position within said enclosure; whereby the foam not only provide a protective cushion for the wound but also a volume for absorbing blood and drainage from the wound, and a medium into which antibiotics can be introduced, and
   c. manually manipulating the enclousre so as to confine the foam between the enclosure and the wound.

* * * * *